US008774560B2

(12) United States Patent
Sugaya et al.

(10) Patent No.: US 8,774,560 B2
(45) Date of Patent: Jul. 8, 2014

(54) SYSTEM FOR MANIPULATION, MODIFICATION AND EDITING OF IMAGES VIA REMOTE DEVICE

(75) Inventors: Kiminobu Sugaya, Winter Park, FL (US); Balaji Gandhi, Tempe, AZ (US); Srikanth Yellanki, Normal, IL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 170 days.

(21) Appl. No.: 12/611,953

(22) Filed: Nov. 4, 2009

(65) Prior Publication Data

US 2010/0077358 A1 Mar. 25, 2010

Related U.S. Application Data (63) Continuation-in-part of application No. 11/813,679, filed as application No. PCT/US2006/000983 on Jan. 11, 2006, now abandoned.

(60) Provisional application No. 60/642,925, filed on Jan. 11, 2005.

(51) Int. Cl.
*G06K 9/54* (2006.01)

(52) U.S. Cl.
USPC ............ 382/305; 382/276; 382/154; 382/128

(58) Field of Classification Search
CPC .................................................... G06T 11/006
See application file for complete search history.

(56) References Cited

U.S. PATENT DOCUMENTS

| | | | | |
|---|---|---|---|---|
| 5,216,596 A | * | 6/1993 | Weinstein | 348/79 |
| 5,297,034 A | * | 3/1994 | Weinstein | 382/128 |
| 5,655,028 A | * | 8/1997 | Soll et al. | 382/133 |
| 5,671,288 A | * | 9/1997 | Wilhelm et al. | 382/128 |
| 5,737,539 A | | 4/1998 | Edelson et al. | |
| 5,793,969 A | * | 8/1998 | Kamentsky et al. | 709/213 |
| 5,836,877 A | * | 11/1998 | Zavislan | 600/407 |
| 5,845,255 A | | 12/1998 | Mayaud | |
| 6,006,191 A | * | 12/1999 | DiRienzo | 705/2 |
| 6,078,681 A | * | 6/2000 | Silver | 382/133 |
| 6,101,265 A | * | 8/2000 | Bacus et al. | 382/133 |
| 6,175,655 B1 | * | 1/2001 | George et al. | 382/257 |
| 6,272,235 B1 | * | 8/2001 | Bacus et al. | 382/133 |
| 6,396,941 B1 | * | 5/2002 | Bacus et al. | 382/128 |
| 6,415,046 B1 | * | 7/2002 | Kerut, Sr. | 382/128 |
| 6,466,690 B2 | * | 10/2002 | Bacus et al. | 382/133 |
| 6,510,241 B1 | * | 1/2003 | Vaillant et al. | 382/154 |
| 6,606,413 B1 | * | 8/2003 | Zeineh | 382/232 |
| 6,674,881 B2 | * | 1/2004 | Bacus et al. | 382/128 |

(Continued)

OTHER PUBLICATIONS

Brinkley et al. Imaging and the Human Brain Project: A review, methods Inf. Med. 2002, vol. 4, pp. 245-260 See entire article.

(Continued)

*Primary Examiner* — Tsung-Yin Tsai
(74) *Attorney, Agent, or Firm* — Timothy H. Van Dyke; Beusse, Wolter, Sanks, Mora & Maire, P.A.

(57) ABSTRACT

Disclosed herein is a system and method for providing remotely accessible medical image data. The system and method allows for increased accuracy and semi-quantitative or fully quantitative data from images by enabling the remote user to select regions of interest on a compressed image, and then conducting quantitative analysis on original images at a central location.

14 Claims, 8 Drawing Sheets

(56) References Cited

U.S. PATENT DOCUMENTS

| | | | |
|---|---|---|---|
| 7,072,840 B1 | 7/2006 | Mayaud | |
| 7,426,475 B1 | 9/2008 | Tangellapally et al. | |
| 7,428,324 B2* | 9/2008 | Crandall et al. | 382/128 |
| 2002/0106119 A1* | 8/2002 | Foran et al. | 382/133 |
| 2002/0177771 A1* | 11/2002 | Guttman et al. | 600/410 |
| 2003/0038798 A1* | 2/2003 | Besl et al. | 345/420 |
| 2003/0101076 A1* | 5/2003 | Zaleski | 705/2 |
| 2003/0163031 A1* | 8/2003 | Madden et al. | 600/300 |
| 2003/0184730 A1* | 10/2003 | Price | 356/39 |
| 2003/0208116 A1* | 11/2003 | Liang et al. | 600/407 |
| 2004/0032980 A1* | 2/2004 | Harman | 382/154 |
| 2004/0052328 A1* | 3/2004 | Sabol et al. | 378/37 |
| 2004/0122790 A1* | 6/2004 | Walker et al. | 707/1 |
| 2004/0141637 A1* | 7/2004 | Bacus et al. | 382/128 |
| 2004/0217956 A1* | 11/2004 | Besl et al. | 345/419 |
| 2004/0252875 A1* | 12/2004 | Crandall et al. | 382/133 |
| 2005/0036667 A1* | 2/2005 | So et al. | 382/128 |
| 2005/0047636 A1* | 3/2005 | Gines et al. | 382/131 |
| 2005/0113960 A1* | 5/2005 | Karau et al. | 700/182 |
| 2005/0210015 A1* | 9/2005 | Zhou et al. | 707/3 |
| 2005/0228250 A1* | 10/2005 | Bitter et al. | 600/407 |
| 2006/0153434 A1* | 7/2006 | Wang | 382/128 |
| 2006/0159325 A1* | 7/2006 | Zeineh et al. | 382/128 |
| 2006/0159367 A1* | 7/2006 | Zeineh et al. | 382/276 |
| 2006/0242159 A1* | 10/2006 | Bishop et al. | 707/10 |
| 2007/0081706 A1* | 4/2007 | Zhou et al. | 382/128 |
| 2008/0232658 A1* | 9/2008 | Sugaya et al. | 382/128 |
| 2009/0326336 A1* | 12/2009 | Lemke et al. | 600/300 |

OTHER PUBLICATIONS

Lancaster et al. Automated Talairach Atlas Labels for Functional Brain Mapping. Human Brain Mapping. 2000 vol. 10, pp. 120-131, entire document.

Buccigrosse et al. Image Compression Via Joint Statistical Characterization in the Wavelet Domain IEEE Transaction on Image Processing. Dec. 1999, vol. 8, pp. 1688-1701.

Koh, distributed, Web-based Microstructure Database for Brain Tissue. Dissertation Submitted to Texas A&M Univ. May 2000, pp. 1-16.

* cited by examiner

FIG. 1a
*Sample sagittal slice of INOS mRNA ISHH. The original scanned TIFF image is 2506 X 1812 pixels and 8.9MB in size.*

FIG. 1b
*Differential pixel images, detected by the image subtraction, between original and after compression using JPEG (A: low compression, B: high compression), while TIFF or PNG did not show difference in this type of image.*

FIG. 2 Dynamic real time 2D image viewer. The panel on the top shows a full slide, and the panel in the bottom is the result of zooming in on a region of interest at the highest resolution possible as shown by the small triangle position on the toolbar (Zoomify)

FIG. 3

Dynamic real time 2D image viewer. The viewer allows user to print the image and also make non destructive user specific annotations which will enable them to save their regions of interest or other notes.

FIG. 4  *Serial 2D image of ISHH for APP gene expression in the rat brain.*

FIG. 5  *Example of the reconstruction of 3D data set from 2D ISHH data.*

FIG. 6

*IMGEM 3D Interactive viewer. The 3D image stack is made of serial 2D images shown in Fig.6. This viewer allows user to preview and rotate the 3D image and to select the slice of interest and open it in the image processing application.*

FIG. 7

IMEGM image processing application ( ) which runs as an applet eliminating any software install on client machine. Using 3D IMEGM viewer user can rotate the 3D image in the preview mode and after selecting the slice of interest, open the image in image processing application. The insets are the histogram and pseudo coloring of the selected region.

SYSTEM FOR MANIPULATION, MODIFICATION AND EDITING OF IMAGES VIA REMOTE DEVICE

RELATED APPLICATIONS

This application is a continuation-in-part of U.S. Ser. No. 11/813,679 filed Jun. 2, 2008, now abandoned which is a U.S. national stage filing of PCT/US06/00983 filed Jan. 11, 2006, which claims the benefit of U.S. Ser. No. 60/642,925 filed Jan. 11, 2005, now lapsed, all of which are incorporated herein in their entireties.

BACKGROUND

A relatively large amount of information is required by doctors, physicians, and medical providers. This information is usually maintained on computers at a medical facility or other central locations. When a practitioner wishes to view and review medical files for patients, the practitioner usually connects to the computer storing the information, such as using a terminal at the facility or a remotely connected computer. However, in today's mobile society, access to a full power computer is not always possible. Practitioners want to be able access information on portable remote devices such as cellular based communication devices or browser based portable devices (iPhones, iPod Touch, etc.).

Unfortunately the processing power of these remote devices, as well as limited memory and other limitations inherent on smaller devices cause difficulty in getting the necessary information in a timely and efficient manner. As such, the inventors have realized that a user needs a way to display and manipulate data viewed in a remote device having limited processing power.

A number of patents exist which relate to medical software for physicians, including, U.S. Pat. Nos. 7,426,475; 7,072,840; 5,737,539; 5,845,255; all of which are incorporated herein by reference. Several projects related to 3D-imaging are TeleMed-VS, 3D-DOCTOR, PACS, and OsiriX. The projects related to 3D-imaging attempt to solve the challenge of medical 3D-imaging by storing large 3D-image files (image files composed of multiple 2D images) and manipulating such files through the use of graphical libraries. OsiriX brings clinical images to the iPhone, however, it does not allow for manipulations.

The above-noted patents and ideas fail to solve the challenge of portability and efficiency because they do not incorporate multiple needs of the physician into one implementation, which increases efficiency. Also, the majority of the patents and ideas do not address the issue of portability, which is essential to efficiency.

The present invention is designed to address these needs.

SUMMARY OF THE INVENTION

The inventors have employed technological advantages of electronic databases in the open source software sector by creating a series of medical images implemented via databases implemented through computer hardware and software to provide a remote image interactive system. The system comprises several advantageous aspects: 1) system contains archive 2D medical images with multiple levels of resolution, and can share information with other researchers 2) by the 2D and 3D image analysis, the system facilitates the comparison of multiple features in the image(s) 3) by 3D reconstruction of the image data, the system enables free rotation of the 3D image and virtual-sectioning of the image set with rotation in any desired plane, 4) the system may include a discussion board (or discussion forum) capability, which is capable of receiving responses or input from users in real-time; and as an additional benefit, the system can optionally be readily edited and updated to reflect the real-time input of online users, 5) the system may also be seamlessly integrated with other currently available online databases and hyperlinks to other data resources on the Internet will be highlighted on the images and easily accessible via the system's user-friendly design and navigation.

According to one embodiment, the invention pertains to a remote image processing system that is a fully interactive, integrated and compatible to any platform. Most of the image databases currently available are built for either windows or mac platform. The present system embodiment is developed as a strictly web based application which is developed in JAVA and/or other cross platform scripts making it truly platform independent. The system supports users to upload or provide links to their image data or any other kinds of medical image data to a central server or servers directly from the website. The system also involves an annotation feature that enables researchers to make non-destructive comments or notes on the images which will enable collaborating researchers to directly access the other researcher's notes on the image without downloading and image data. The system allows for quantitative image processing which is enabled by the thin client 3D application by doing all the image processing on the quantitative image (e.g. TIFF) in the server, thereby overcoming the hurdles posed by the limitations of internet data transfer protocols.

Conventional image databases do not accomplish real time manipulation of 3D data set via the remote browser. Due to the limitations of Internet traffic speed and scripting in Internet language, for example JAVA, the results are far behind from the image processing that occurs on the computer on which the image is saved. Furthermore the nature of the JPEG or GIF image file format used in the web browser diminishes a possibility of quantitative analysis of the image data. The system embodiment addresses these problems, which always exist with distribution of experimental data through the Internet by advanced scripting and analysis of data set on the server with manipulation of the image on the client.

It is to be understood that the foregoing general description and the following detailed description are exemplary and explanatory only and are not to be viewed as being restrictive of the present, as claimed. These and other objects, features and advantages of the present invention will become apparent after a review of the following detailed description of the disclosed embodiments and the appended claims.

DETAILED DESCRIPTION

In reviewing the detailed disclosure which follows, and the specification more generally, it should be borne in mind that all patents, patent applications, patent publications, technical publications, scientific publications, websites, and other references referenced herein are hereby incorporated by reference in this application in order to more fully describe the state of the art to which the present invention pertains.

In one embodiment, the subject invention is directed to a system for providing remotely accessible medical image data. The system allows for increased accuracy and semi-quantitative or fully quantitative data from images by enabling the remote user to select regions of interest on a compressed image. Quantitative analysis of the selected region is conducted on original images at a central database location on a central server and then the analysis results are conveyed to the remote user. The system may provide internet based software tools for the extraction of functional information from gene expression images and also to act as a repository for gene expression image data.

Those skilled in the art should appreciate that the present invention may be implemented over a network environment. That is, the remote user may be a client on a number of conventional network systems, including a local area network ("LAN"), a wide area network ("WAN"), or the Internet, as is known in the art (e.g., using Ethernet, IBM Token Ring, or the like). Typically, the remote user accesses the system via the internet. As will be discussed below, embodiments of the subject invention will allow, for the first time, quantitative analyses and 3D manipulations directed by remote users via small bandwidth connection means, such as the internet.

As used herein, the term "processor" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information.

Functions of a system having a processor as described herein can be implemented by computer-readable program code modules. These program code modules may be provided as part of firmware and/or computer-readable memory, or otherwise provided to a processing module of a general purpose computer (e.g. server), special purpose computer, embedded processor or other programmable data processing apparatus to produce a machine, such that the program code modules, which execute via the processing module of the computer or other programmable data processing apparatus, or as part of firmware, create means for implementing specified functions.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing predetermined functions.

The image data implemented by the system may include images such as those obtained from, but not limited to, x-ray, magnetic resonance imaging (MRI), pet scan, ultrasound, optical coherence topography (OCT), intravascular ultrasound (IVUS), fluoroscopy, as well as images of histological sections. See, e.g., U.S. Patent Publication 20080288450. Image Registration techniques may be used when needed to align the images with each other. Spatial transformations alter the spatial relationships between pixels in an image by mapping locations in an input image to new locations in an output image. In Image registration typically one of the datasets is taken as the reference, and the other one is transformed until both datasets match. This is important as images must be aligned to enable proper 3D reconstruction for quantitative analysis. Especially with respect to histological section images, using the Matlab Image Processing Toolbox, select points in a pair of images (using points from external Marker-based Automatic Congruencing technique which is described in Example 8) are interactively selected and the two images are aligned by performing a spatial transformation. In a specific embodiment, the system includes a registration module that provides an affine registration, i.e. it determines an optimal transformation with respect to translation, rotation, anisotrope scaling, and shearing.

A true image format is desired to accurately store an image for future editing. Choosing the most appropriate true image format from dozens of existing formats is important for the success of certain system embodiments. On a computer monitor, images are nothing more than variously colored pixels. Certain image file formats record images literally in terms of the pixels to display. These are called raster images, and they can only be edited by altering the pixels directly with a bitmap editor. Vector image files record images descriptively, in terms of geometric shapes. These shapes are converted to bitmaps for display on the monitor. Vector images are easier to modify, because the components can be moved, resized, rotated, or deleted independently. Every major computer operating system has its own native image format. Windows and OS/2 use the bitmap (BMP) format, which was developed by Microsoft, as the native graphics format. BMP tends to store graphical data inefficiently, so the files it creates are larger than they need to be. Although Mac OS can handle any kind of format, it is preferential to the PICT format, which more efficiently stores graphical data. Unix has less of a standard, but X Windows and similar interfaces favor XWD files. All of these formats support full 24-bit color but can also compress images with sufficiently fewer colors into 8-bit, 4-bit, or even 1-bit indexed color images. However, one disadvantage of file compression is the occasional loss of image quality. Tagged image file format (TIFF) is a "loss-free", 24-bit color format intended for cross platform use, and tends to be accepted by most image editors on most systems. TIFF can handle color depths ranging from one-bit (black and white) to 24-bit photographic images. Although, like any standards, the TIFF developed a few inconsistencies along the way; but nevertheless, this format is a good format to store the original 2D data of certain system embodiments.

Since, in one embodiment, the system is implemented on the World Wide Web, graphics formats have to be compatible with web browser. Current web browsers can handle graphics interchange format (GIF), Joint Photographic Experts Group (JPEG) and Portable Network Graphic (PNG). Most images and backgrounds on the web are GIF files. This compact file format is ideal for graphics that use only a few colors, and it was once the most popular format for online color photos. However, GIF has lost some ground to the JPEG format, due to the higher quality of JPEG for handling photo images. GIF images are limited to 256 colors, but JPEGs can contain up to 16 million colors, and they can look almost as good as a photograph. JPEG compresses graphics of photographic color depth better than competing file formats like GIF, and it retains a high degree of color fidelity. This makes JPEG files smaller and therefore quicker to download. Compression dynamics for a JPEG file can be defined, but since it is a format prone to lose image quality, the smaller we compress the file, more color information will be lost.

Figure 1A:
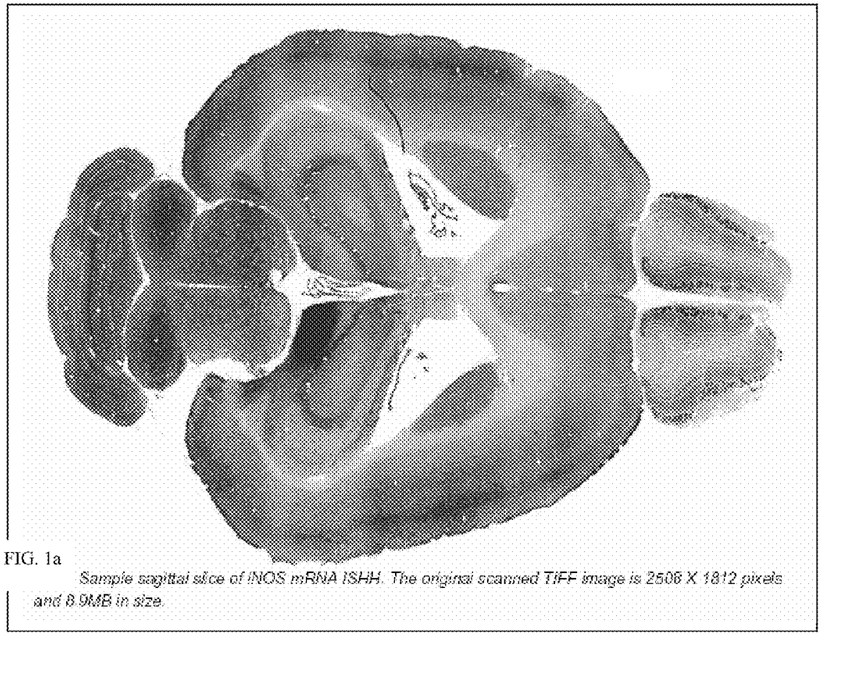
FIG. 1a shows a sample sagittal slice of iNOS mRNA ISHH. The original scanned TIFF image is 2508×1812 pixels and 8.9 MB in size.
Figure 1B:
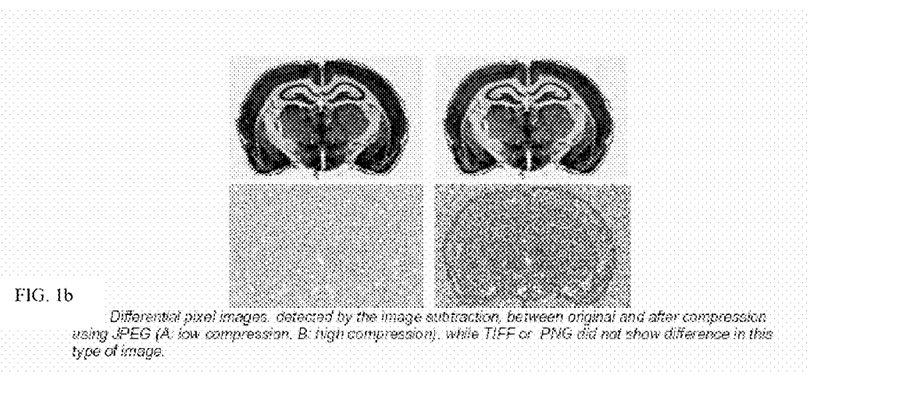
FIG. 1b Differential pixel images, detected by the image subtraction, between original and after compression using JPEG (A: low compression, B: high compression), while TIFF or PNG did not show difference in this type of image.

FIG. 1 shows differential images between original and after compression using these three formats and the resulting file sizes. The original image data (284 Kb, 654×438 pixels) is 8-bit gray scale image, GIF (296 Kb) and PNG (268 Kb) show no loss of image information, but JPEG shows degradation of image in low compression (152 Kb) and high compression (24 Kb) modes (FIG. 1). If the complexity of the original image is low (284 Kb), GIF, JPEG low compression, JPEG high compression and PNG compress the file size to 172 Kb, 92 Kb, 16 Kb and 164 Kb respectively. By far the most promising "loss-free" format is PNG. For ease of calling up images over the Internet at today's limited bandwidth, JPEG is a good image format to use whenever quantitative information is not required.

The 2D data is presented as interactive images for fast initial display and on demand viewing of fine details. The images can be viewed without any large download. Web site visitors can interactively zoom-in and explore the images in real time. The user can then choose the precise section to manipulate for further analysis without using any software that needs to be downloaded and installed. The inventors incorporated an interactive multithreaded image processing and analysis application written in java (e.g. ImageJ). The system may incorporate a powerful, standards-based, nondestructive annotation system that allows registered users to make both simple, intuitive annotations, which will enable them to save their regions of interest or other notes and these annotations will be non destructive and user specific.

In one embodiment, medical images are archived as TIFF files. Typically, the image consists of 690×465=320,850 pixels=480 Kb (if it is 8 bit then 320 Kb). The image files will be converted into the web image file format, depending on the complexity of the image (for example, a 320 Kb TIFF image will be compressed to 180 Kb-325 Kb in GIF format and 160 Kb-285 Kb in PNG format). If the JPEG format is used, the file size will vary according to the complexity of the image and the quality of the compression (for example, a 320 kb TIFF image will be compressed to 17 Kb-165 Kb, but the reproducibility of the image would be very low). Thus, in a more specific version, the system uses high compression JPEG images for indexing, medium compression JPEG format to display qualitative images, and TIFF format to send quantitative images.

Example 1

Setup for Working 2D Image Data Set

The image files will be converted into the web image file format. The file size after compression will depend on the complexity of the image. 2D medical images of acoronal, sagittal and horizontal anatomical section will be stored in low or uncompressed JPEG format files and at the original resolution (1 pixel=20 μm×20 μm). From these images, low resolution JPEG medium compressed files (100×148 pixels) will be produced and stored for the index. Each file will be named by image file characteristics, and resolution with file format extension. In an example of a brain sectioning, one set of the image data from one brain section will have a file size of ~2.7 MB. Since ~1000 sections (20 μm) will be sliced from one rat brain, one set of the 2D image data from one brain will occupy ~2.7 GB of disk space.

The 2D image data will be able to be retrieved by two modes: (1) Visual Selection Mode (VSM). In this mode, the user can select the target section by positioning the computer mouse on the whole image model, side views for the coronal or horizontal slices and top views for the sagittal slices. As the user moves the pointer along the area, thumbnail index images in image characteristics will be dynamically changed. When the user clicks on the desired selection, a new browser window with multiple images will open (the user can select the number of images (9, 16 and 25), and can choose between ISHH and Nissl stain images). Next, the user can select the exact images to be retrieved by clicking on the multiple images. The selected images will be displayed in a new browser window.

VSM allows the user to visually select entire 2D image data with a small whole brain model (80 selection points in a 160 pixel image). The download traffic time, which includes a low compressed JPEG image as the final retrieved image, will be <0.85 sec at 300 KB/sec transfer rate. (2) The second retrieval mode is a database search based on type of images, file name, anatomical region, gene, species, cutting plane etc to be displayed in a new browser window. The manipulation of the brain sectioning images can be applied to other types of medical images and anatomical regions.

Tiling

Figure 2:
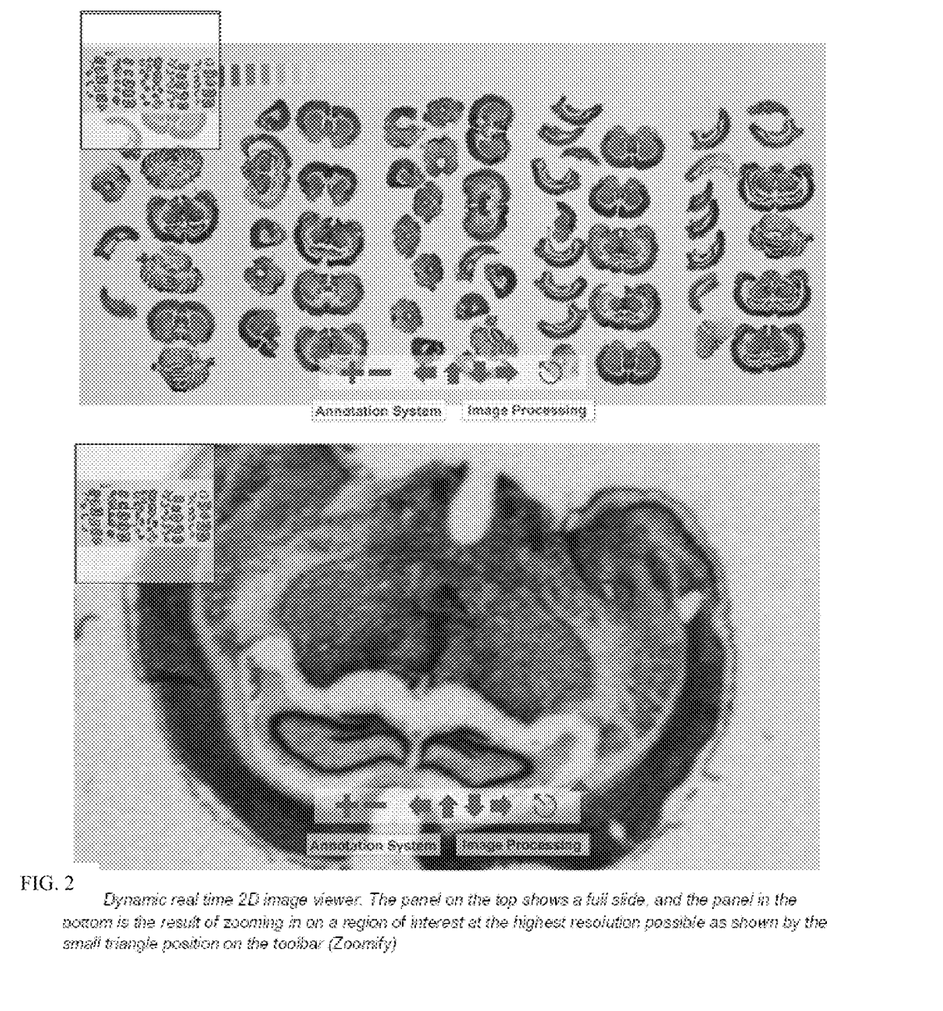
FIG. 2 represents a screen shot of a dynamic real time 2D image viewer according to one embodiment of the subject invention. The panel on the top shows a full slide, and the panel in the bottom is the result of zooming in on a region of interest at the highest resolution possible as shown by the small triangle position on the toolbar.

Remote users can interactively zoom-in and explore the images in real time. The 2D image is converted in to a file format for incremental access. The system 2D Viewer is then able to display any view of the anatomical region without delivering any unneeded, undisplayed image data. The 2D image is copied several times at different resolution levels— from the original source resolution down to a thumbnail. Each of these levels is cut into many small tiles. All the tiles from all the levels are then incorporated into a single file system along with an index of the exact location in the file. This file is pyramidal—that is, like a pyramid, stacked from a thumbnail down to the highest resolution, level upon level. When the new file is viewed, the system 2D Viewer uses the index to request the lowest resolution tiles from the Web server and displays the thumbnail. Each pan and zoom causes a request for only a small additional number of tiles—those for the part of the image panned to, at the level of zoom desired. No tiles are ever delivered unless required for the current display—or for a display that is anticipated to immediately follow (intelligent pre-fetching). These requests for image data are all made via standard HTTP 1.1 Internet protocol. The only difference is that the Web server is providing parts of image files rather than entire image files. The user can interactively zoom in to the region of interest (FIG. 2) or the slice, and select ROI, and open the selected ROI in a different window with the image processing application to do further analysis. The download traffic time, which includes low or uncompressed JPEG image as the final retrieved image, will be <2 sec at 300 KB/sec transfer rate.

Example 2

Manipulation and Analysis of the 2D Image Data

Figure 3:
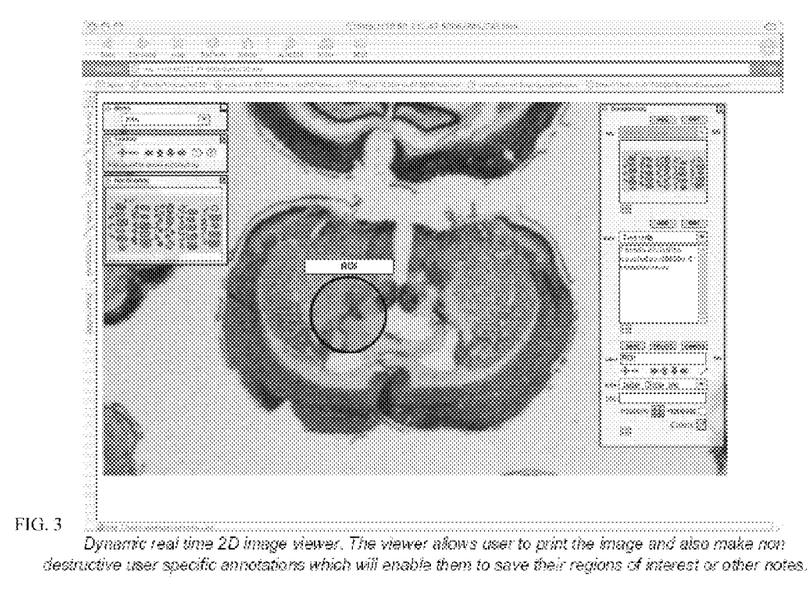
FIG. 3 represents a screen shot of a dynamic real time 2D image viewer according to an embodiment of the subject invention. The viewer allows user to print the image and also make non-destructive user specific annotations which will enable them to save their regions of interest or other notes.

The images are displayed as interactive images which the user can zoom in real time without any delay. A powerful, standards-based, nondestructive annotation system is also provided that allows registered users to make both simple, intuitive annotations, which will enable them to save their regions of interest or other notes and these annotations will be non destructive and user specific (FIG. 3). From the system 2D viewer the user will be able to print the image as displayed (the specific region of interest) for reference purposes. The image-processing program may incorporate open source programs such as ImageJ written by Wayne Rasband of the Research Services Branch, National Institute of Mental Health. ImageJ will run on Java environment as an online applet. The image processing program will calculate the area and pixel value statistics of user defined selections, or region of interest (ROI). It performs geometric transformations such as scaling, rotation and flips; and it also supports standard image processing functions such as drawing, zoom, application of user-defined LUT modification, thresholding, making binary, contrast and brightness manipulation, sharpening, smoothing, and other filtering. Since ImageJ is based on an open architecture; addition of user-written plug-ins make it possible to solve almost any image processing or analysis problem.

Furthermore, ImageJ supports any number of windows simultaneously with the only limitations being the users available RAM in the client. The inventors provide a add-on to this software, which allows for remote manipulation of image data by system users. Thus, users will be able to manipulate images in the preview mode, and then send a request to the server for the final high resolution image. This procedure may not be so important for retrieving single 2D image data, but for the quantitative analysis of multiple 2D image or 3D data sets, this capability is critically important. Manipulation of multiple 2D or 3D image data will involve heavy traffic of data over the network. Without an integrated preview mode, due to the limitations of current network transfer rates, the manipulation of multiple image data is burdensome and impractical.

Example 3

Interactive Multiple 3D Image Datasets from the 2D Image Dataset

The data handling concept, using the system's 2D viewer preview mode, as explained above, is important for manipulation of the 3D data. If the users have to download 960 MB of data before they are able to begin any image manipulations, this might require more than 50 min, using a 300 KB/sec network connection. This is not feasible. In order to circumvent this problem, the inventors use a wire frame or surface model or a small low-resolution data set (or preview image) to manipulate image data in the system's preview mode, and then transfer the final results in JPEG or PNG. The first steps of 3D manipulation will be made by the combination of Java Applets and Servlets. Once the user gets the plane of interest in the 3D preview mode, the user can obtain a higher resolution 2D image from the 3D by performing a virtual slicing and then do the image processing. Whatever processing that the user performs on his client on the 2D JPEG image will be recorded automatically, and when the user is done he can get the quantitative dataset of the image with all the image processing operations performed on the original TIFF 2D plane obtained from the 960 MB TIFF stack. This operation is made in combination of XML and Java Servlets.

Example 4

Figure 4:
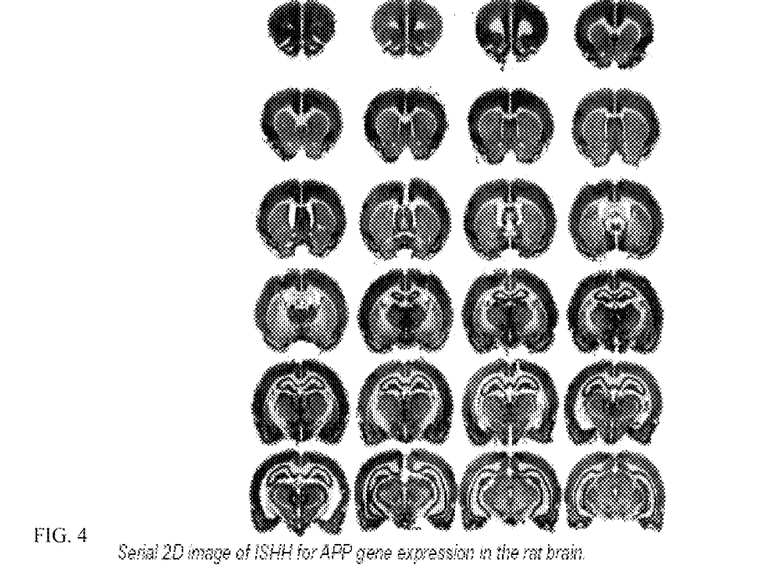
FIG. 4 represents serial 2D image of ISHH for APP gene expression in the rat brain.
Figure 5:
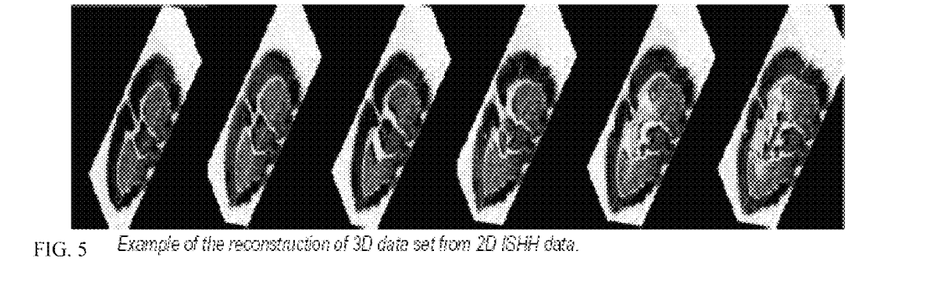
FIG. 5 represents an example of the reconstruction of 3D data set from 2D ISHH data.
Figure 6:
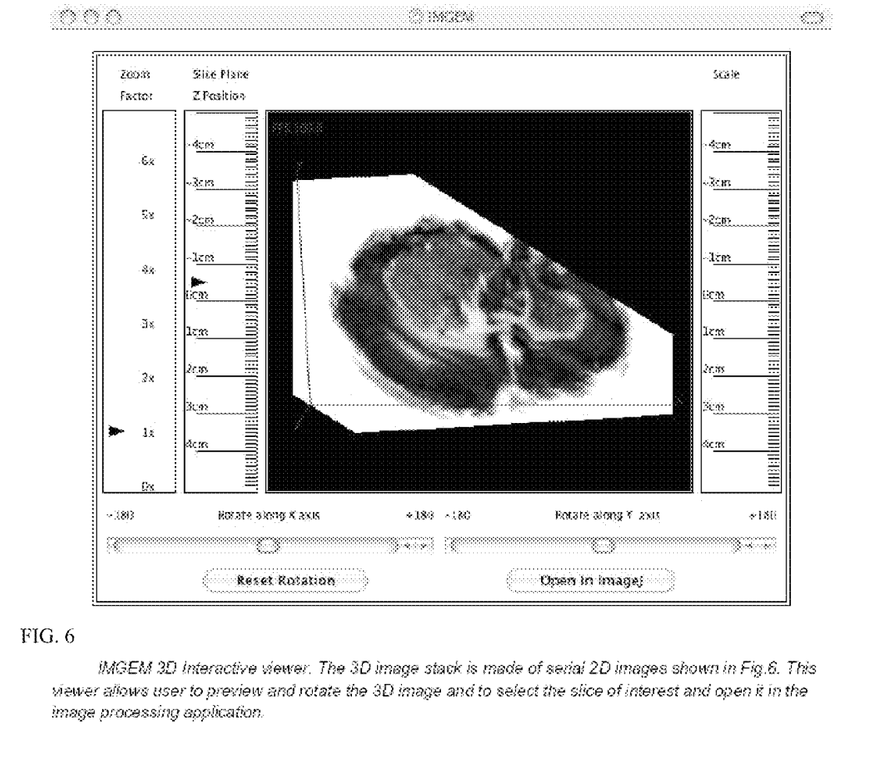
FIG. 6 is a screen shot of a 3D interactive viewer according to one embodiment of the invention. The 3D image stack is made of serial 2D images shown in FIG. 6. This viewer embodiment allows user to preview and rotate the 3D image and to select the slice of interest and open it in the image processing application.

Reconstruction of 3D Data Set from 2D Image Data 2D coronal serial section images, in TIFF format, are reconstructed into 3D data sets using NIH image stack command. Since the brain slices are sectioned at 20 μm and the ISHH and Nissl-stain images are taken at 1270 dpi×1270 dpi (1 pixel=20 μm×20 μm), voxel of the reconstructed 3D data set will be 20×20 μm×20 μm. Data size will be 320 MB (465×690×1000 voxels) and 960 MG (465×690×1000 voxels×RGB), respectively. FIG. 5 demonstrates a sample of the construction of a 3D data set from 2D image data (FIG. 4). In this case, a cut was made through the bottom half of the 3D data to illustrate a horizontal cut of the brain. In this example, since there are only images from every 12 serial sections, the thickness by interpolation was added. The provided horizontally-sliced image is not the best quality, but the 3D data set may be constructed from every serial section without interpolation; thus, the horizontally-sliced images will be the same high quality as coronally-sliced images. Though this example utilizes tissue section slices to illustrate the embodiment, the above techniques can be used for any suitable medical image.

Example 5

Manipulation and Analysis of the 3D Data Set with Integration of 2D Image Data

Manipulation of 3D image in real-time on the client terminal will be a challenge if the 3D data set is localized. It takes about 18 min to transfer a typical 3D data set (320 MB), therefore manipulation of local data is not practical using currently available network technology.

Thus, the inventors used thin client technology to facilitate real-time manipulation of the 3D data set. The user can manipulate the 3D view by positioning of the mouse around the model; and if it is necessary, the user can make dissections by re-slicing. Once the view is satisfactory, the user can send a command to retrieve the final image. The download traffic time, which includes a rendered 3D image in low compressed JPEG format as the final retrieved image, will be <1.5 sec at 300 KB/sec transfer rate.

In contrast to a 2D Visualizing system, the 3D Visualizing system needs to be highly interactive to offer the user a smooth experience while viewing the 3D Image. Web scripting languages like JavaScript, VBScript do not have the functionality to display 3D Images. Browser plug-ins like Shockwave, Real Player and Windows Media Player have the ability to display 3D but only as a movie, which is not interactive.

Hence a programming language that is web enabled and highly interactive was needed. Though not to be construed as limiting, the inventors choose to use Java as the programming language for the 3D visualization system, which introduced the concept of Applets. An Applet is a software component, which can run in the context of a web browser. An Applet is lightweight, platform independent and is backed by a powerful programming language—Java. Other types of programming language could be used.

The inventors designed a 3D Visualizing system embodiment based upon Orion Lawlor's SliceViewer Component. The 3D Visualizing system is capable of displaying the 3D reconstructed images, which are in RAW format. But as is mentioned above, the complexity of this system is increased because of the volume of data (100 MB-500 MB) being handled.

The user may not be patient enough to download such a huge volume of data and even if he does, loading this data on his machine depends upon the computing power and resources of the client machine. The best way to overcome this problem is to display a preview image in the client machine. The inventors created scaled down versions of the actual images, which are approximately 100 KB-2 MB in size. This is the optimal size, which can be easily downloaded and displayed in the client machine. This is shown in FIG. 4.

This image loads up quickly in the client machine. This image can be rotated in 3D space and the user can zero-in on the slice he wants to analyze further. When the user selects his slice of interest, he can open the image in an Image Processing application. The problem here is that this image is good for 3D Rotation and Manipulation but it is not good enough for image processing and analysis. The same slice can be obtained from the original 3D Image stack for Image Processing and Analysis. But the size of the slice obtained can be huge and it may cause the same problems again viz.: (1) Network bandwidth and (2) Client machine's computing power. These issues are addressed by creating an image stack, which is smaller in size than the original stack but is good enough to support image processing. This stack is used to obtain a high-resolution stack, which can be used to do image processing and analysis on the client. When the user selects a slice of interest after manipulating the preview 3D image he can request for a higher resolution stack. The parameters resulting from these manipulations are: (1) Angle of Rotation along X-axis; (2) Angle of Rotation along Y-axis; (3) Slicing Position and (4) Magnification.

Figure 9:
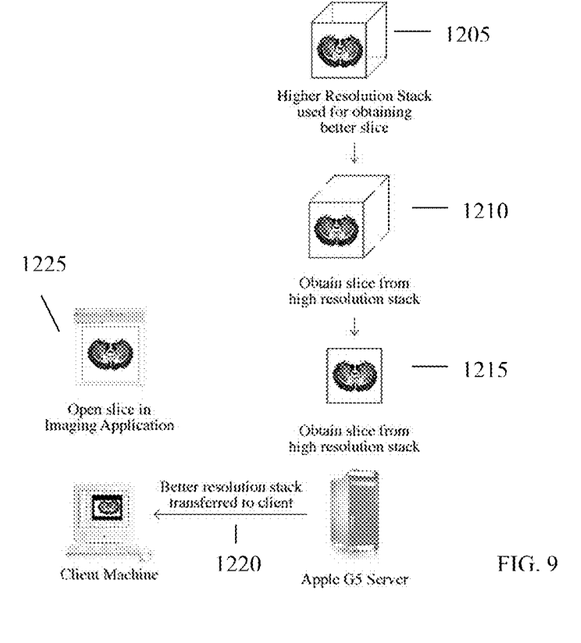
FIG. 9 shows a diagram of an image manipulation method embodiment.
Figure 10:
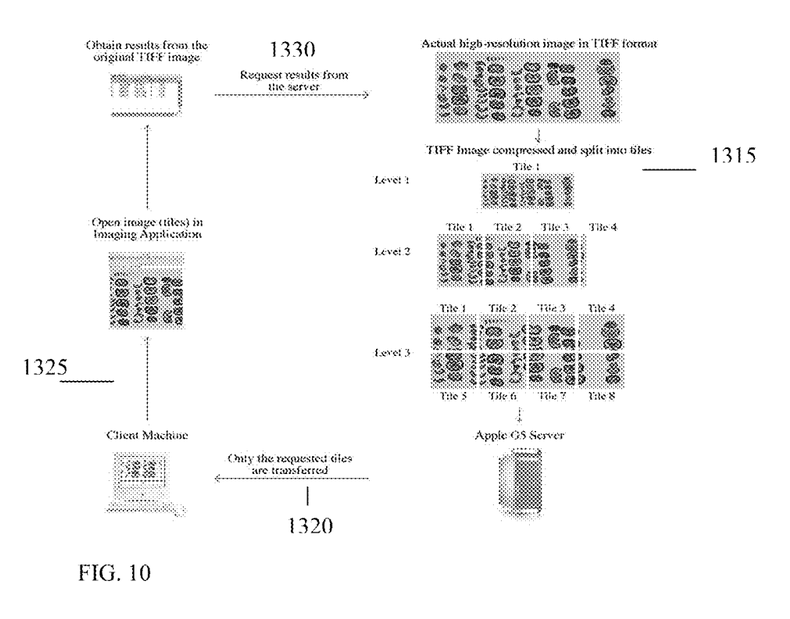
FIG. 10 shows a diagram of an image manipulation method embodiment.

These parameters are sent as plain text to the server as shown in FIG. 9. The high-resolution slice is extracted from the high-resolution image stack using these parameters. This image is sent to the client over http protocol, which is opened in an Image Processing Application as shown in FIG. 10.

An example of a system that enables users to manipulate 3D models of the brain in real-time, which employs HTML and applet is demonstrated at http://imgem.ucf.edu/3D_dataarchive.htm. When users are satisfied with the manipulation in preview mode, they can retrieve the final high quality image. The inventors started with an HTML/Java applet system, and gradually integrated the 3D portion of IMGEM into VRML with Java 3D. In this way, IMGEM will be functional and ready for the upcoming future transitions to real-time manipulation of 3D data, when network speeds are increased. This system can function in manipulating all different types of images.

Figure 7:
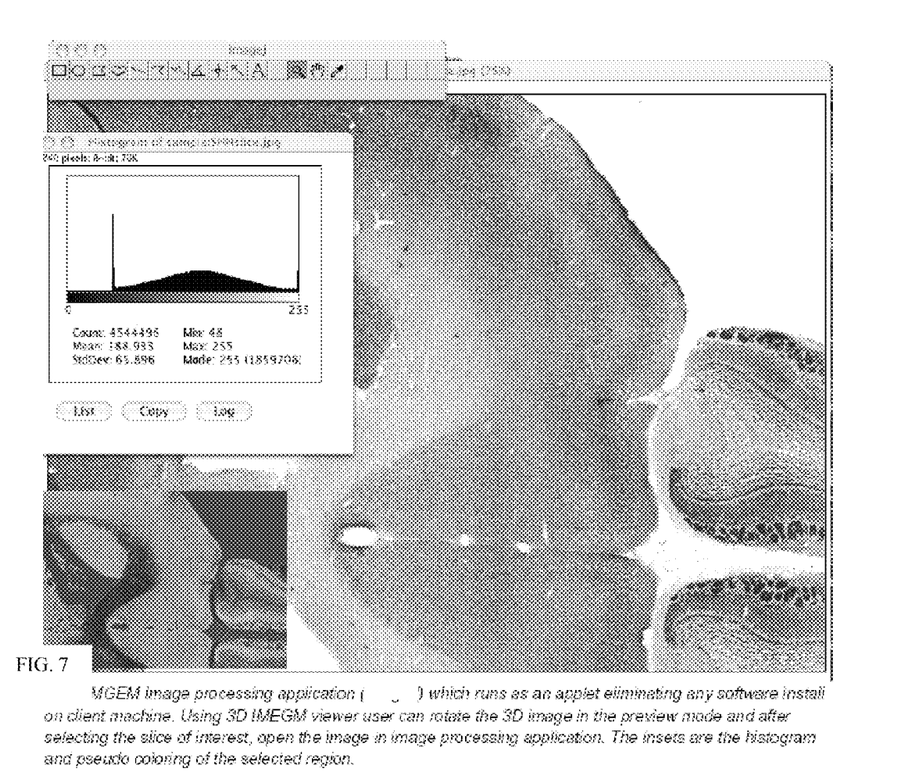
FIG. 7 image processing application which runs as an applet eliminating any software install on client machine. Using the 3D viewer the user can rotate the 3D image in the preview mode and after selecting the slice of interest, open the image in image processing application. The insets are the histogram and pseudo coloring of the selected region.

IMGEM's 3D view manipulation allows users to rotate the 3D image stack in the preview mode, which is a low resolution image 3D image of the original image data. IMGEM 3D viewer allows the user to slice the 3D data at any vantage point. Selected areas of the 3D data set can be retrieved as serial 2D sections to display. The 2D virtual slice obtained by the user is of medium resolution, which eliminates the need for downloading of large amounts of data to the client machine. The 2D section is opened in the integrated image processing application (FIG. 7) and whatever processing that the user performs on his client on the 2D JPEG image will be recorded automatically. When the user is finished, he can obtain the quantitative dataset of the image from the server, with all the image processing operations performed on the original TIFF 2D plane obtained from the 960 MB TIFF stack. The original data may then be sent to the client machine in a zip format, for example, which allows for faster download.

In addition to dealing with the issue of network bandwidth and processing power on the client machine, the inventors have realized that dealing with the shear size of the original image stack is an issue that must also be addressed. Opening such a huge image is a time consuming and memory intensive operation. For this reason, as discussed above, the loading and manipulation of this image is kept in the server. This Image Processing Application is similar to the one, which is described in Example 2 above. This application can communicate with the server when the user performs the processing and analysis and returns the results from the original image stack. But there is one important difference between the two systems.

Figure 8:
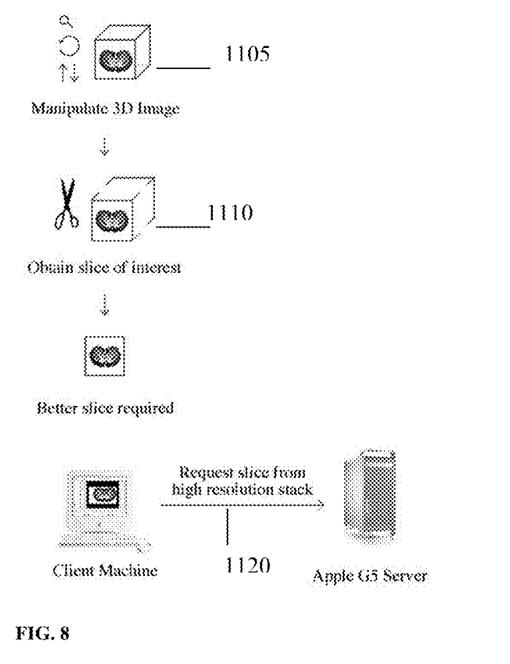
FIG. 8 shows a diagram of an image manipulation method embodiment.

Whereas for the 2D System the quantitative image is available in TIFF format, the 3D System stores it in stacked image format (RAW). Hence the Server-side processing and analysis system has the additional task of retrieving the proper slice of interest from this image stack. After doing this, the results of any processing and analysis conducted by the user on the client can be repeated with this slice in the server and the results can be returned to the user. This interaction is shown in FIG. 8.

Retrieving the slice of interest from the original image stack (100 MB-500 MB) becomes a complex process due to the memory occupied by the image. Even with the high-end resources of the server, the inventors have experienced a number of problems in implementing this system embodiment. In particular, the inventors realized and addressed the following specific problems: (1) Data structure limitations; (2) Java's File operations and (3) Storage of retrieved values. We discuss these problems and the solutions in detail in the following sections.

Data structure limitations: Loading the original stack into 3D arrays (like was done for the preview image stack) is not possible due to limitations imposed by the Java Programming Language (which is used to develop the Server-side Image Analysis module). The size of the arrays that can be created depends on the memory allocated to the JVM—Java Virtual Machine. The Java Virtual Machine is software that converts intermediate Java Code into Machine Language code and executes it. Loading such a large amount of data for the extraction of a slice, which is less than 5% in size of the total image stack, is not reasonable and practical. The inventors created a method to compute the file locations in the image stack where the pixel values for the slice of interest are located. After obtaining the list of file locations where the required pixel values are located, these location values are sorted in ascending order. The image stack file is traversed sequentially (as opposed to a random access if the file locations are unknown) and only the required pixels are loaded into memory.

Java's File operations: As already mentioned embodiments of the subject invention employ, the Java Programming Language for the Server-side Image Analysis module. Java Servlets are the link between this Analysis module and the Visualizing system. Servlets are Java applications, which can run in a web-server or an application-server, perform server-side processing and provide dynamic content to the client. Since they are written in Java, they are portable between servers and operating systems. Java's platform independency is achieved using interpreted byte-code operations. The source code is first compiled into byte-code (intermediate code). This code is platform independent. This code can then be interpreted by the JVM (Java Virtual Machine) for the specific platform. The file I/O, which we mentioned in the previous section, suffers due to interpreted byte-code operations. To overcome this problem, the inventors employed native C++ code to perform the file I/O operations.

Storage of retrieved values: After obtaining the file locations and the associated pixel values, the inventors realized a problem with efficient storage of these values. The inventors realized that a data-structure was needed that could store key-value pairs ([file location, pixel value]), have an efficient look-up time (order of 1) and have a huge storage capacity (without loss of performance). The inventors tried a hashtable data-structure, which is readily available in Java. But the Hashtable available in Java is a Generic Implementation, which can hold all types of objects. The problem with this implementation is that it is designed to hold objects due to which its performance declines with increase in size. To overcome this problem, the inventors devised a customized hashtable, which holds only integer values and is implemented using numerical arrays.

REFERENCES

1. Hecksher-Sorensen, J. and Sharpe, J., 3D confocal reconstruction of gene expression in mouse, Mech Dev, 100 (2001) 59-63.
2. Louie, A. Y., M. M. Huber, et al. (2000). "In vivo visualization of gene expression using magnetic resonance imaging." Nat Biotechnol 18(3): 321-5.
3. Jacobs, R. E., Ahrens, E. T., Dickinson, M. E. and Laidlaw, D., Towards a microMRI atlas of mouse development, Comput Med Imaging Graph, 23 (1999) 15-24.
4. Streicher, J., Weninger, W. J. and Muller, G. B., External marker-based automatic congruencing: a new method of 3D reconstruction from serial sections, Anat Rec, 248 (1997) 583-602.
5. Streicher, J., Donat, M. A., Strauss, B., Sporle, R., Schughart, K. and Muller, G. B., Computer-based three-dimensional visualization of developmental gene expression, Nat Genet, 25 (2000) 147-152.
6. Anderle, P., Duval, M., Draghici, S., et al. (2003) Gene expression databases and data mining. Biotechniques suppl, 36-44.
7. Nissanov J., and McEachron D. L. (1991) Advances in Image Processing for autoradiography. J. Chem. Neuroanot. 4, 329-342.
8. Nissanov J., Gertrand L., and Tretiak O. (2001) Cryosectioning distortion reduction using tape support. Microsc. Res. Tech. 53, 239-240.
9. William, B., Jonathan, N., (2003) A guide to building image Centric Databases, Neuroinformatics, 359-78
10. Gustafson C., Tretiak O., et al. (2004) Design and implementation of software for assembly and browsing of 3D brain atlases. Comput Methods Programs Biomed., in press.
11. Franklin, K. B. J. and Paxinos, G. (1998) The mouse brain in stereotaxic coordinates, 2nd ed., Academic Press, San Diego.
12. Toga, A. W., Santori, E. M., Hazani, R., and Ambach, K. (1995) A 3D digital map of rat brain. Brain Res. Bull. 38, 77-85.
13. Davidson. D., Bard, J., et al. (1997) The mouse atlas and graphical gene expression database. Seminars Cell Dev. Biol. 8, 509-517.

BACKGROUND REFERENCES

U.S. Patent Publication 2004/0199544
U.S. Patent Publication 2004/0119759

While a number of embodiments of the present invention have been shown and described herein in the present context, such embodiments are provided by way of example only, and not of limitation. Numerous variations, changes and substitutions will occur to those of skilled in the art without departing from the invention herein. For example, the present invention need not be limited to best mode disclosed herein, since other applications can equally benefit from the teachings of the present invention. Accordingly, it is intended that the invention be limited only by the spirit and scope of the appended claims in accordance with relevant law as to their interpretation.

What is claimed is:

1. A method of providing to remote users a quantitative analysis of image data comprising:
   providing an image database that is accessible remotely via an internet connection by a remote user, wherein said image database comprises a plurality of non-compressed 2D images from an anatomical location;
   displaying to said remote user a 3D reconstruction of the anatomical location from the plurality of non-compressed 2D images, the 3D reconstruction having a lower resolution than the plurality of non-compressed 2D images;
   presenting to said remote user the option of rotating of said 3D reconstruction and virtual-sectioning of said 3D reconstruction in any plane;
   presenting to said remote user the option of selecting a region of interest in said 3D reconstruction;
   providing to said remote user a 2D image of interest corresponding to a virtual-section of said 3D reconstruction at a selected plane, said 2D image having a higher resolution than the 3D reconstruction;
   presenting to said remote user the option of performing one or more image processing techniques on said 2D image of interest;
   calculating pixel value statistics on said 2D image of interest based on at least one of the plurality of non-compressed 2D images; and
   providing to said remote user said pixel value statistics;

wherein said image database comprises an archive of 2D images with multiple levels of resolution, and.

2. The method of claim 1, wherein said non-compressed images in said image database comprise TIFF images.

3. The method of claim 1, wherein said anatomical location is a brain.

4. The method of claim 1, further comprising providing said remote user an option of annotating upon a selected image and displaying said annotating to a second remote user.

5. A remotely interactive medical image management and viewing system comprising:
- a database comprising a plurality of non-compressed 2D medical images;
- a processor; and
- a computer program product for assisting interactivity between said system and a remote user via an internet connection, said computer program product comprising:
  - a computer readable first program code module for causing said processor to display to said remote user a selection of low-resolution images of said plurality of non-compressed images;
  - a computer readable second program code module for causing said processor to present to said remote user an option to select at least one of said selection of low-resolution images;
  - a computer readable third program code module for causing said processor to display to said remote user a compressed image corresponding to a low-resolution image selected by said remote user;
  - a computer readable fourth program code module for causing said processor to present an option of selecting a region of interest of said selected compressed image; and
  - a computer readable fifth program code module for causing said processor to present an option to said remote user of annotating said selected compressed image;
  - a computer readable sixth program code module for causing said processor to split a compressed image into tiles;
  - a computer readable seventh program code module for causing said processor to present an additional number of tiles over a network to said remote user as a greater degree of resolution is desired; and
  - a computer readable eighth program code module for causing said processor to create a 3D reconstruction of at least a subset of said 2D medical images; a computer readable ninth program code module for causing said 3D reconstruction to rotate upon input from said remote user and an tenth program code module for causing said processor to create a virtual-section of said 3D reconstruction in any plane as inputted by said remote user, wherein said virtual-section comprises a 2D image having a higher resolution than said 3D reconstruction.

6. The system of claim 5, wherein said plurality of non-compressed images comprises a stack of TIFF images.

7. The system of claim 6 further comprising a computer readable eleventh program code module for causing said processor to identify a TIFF image from said TIFF stack corresponding to a low-resolution image selected by said remote user.

8. The system of claim 5, wherein said compressed image is a JPEG image.

9. The system of claim 5 further comprising a computer readable twelfth program code module for causing said processor to present an option to zoom into said region of interest.

10. The system of claim 9 further comprising a computer readable thirteenth program code module for causing said processor to download tiles corresponding to said region of interest at a selected zoom level.

11. A remotely interactive medical image management and viewing system comprising:
- a database comprising a plurality of non-compressed 2D medical images;
- a processor; and
- a computer program product for assisting interactivity between said system and a remote user via an internet connection, said computer program product comprising
  - a computer readable first program code module for causing said processor to create a 3D preview image based on at least a subset of said 2D medical images but having a lower resolution than base non-compressed 2D medical images;
  - a computer readable second program code module for causing said processor to display to said remote user said 3D preview image;
  - a computer readable third program module for causing said 3D preview image to rotate upon input from said remote user; and
  - a computer readable fourth program code module for causing said processor to create a virtual-section of said 3D preview image in any plane as selected by said remote user, wherein said virtual-section comprises a 2D image having a higher resolution than said 3D preview image.

12. The system of claim 11, further comprising a computer readable fifth program code module for causing said processor to present an option to said remote user of annotating said virtual-section.

13. The system of claim 12, further comprising a computer readable sixth program code module for causing said processor to display said annotating to another remote user.

14. The system of claim 11, wherein said non-compressed 2D medical images are TIFF images.

* * * * *